United States Patent [19]
Austin

[11] Patent Number: 5,707,594
[45] Date of Patent: Jan. 13, 1998

[54] PATHOGEN CONTROL SYSTEM

[76] Inventor: Terrance Austin, P.O. Box 3485, San Dimas, Calif. 91773

[21] Appl. No.: 646,027

[22] Filed: May 7, 1996

[51] Int. Cl.⁶ ................................. B01J 19/12
[52] U.S. Cl. ........................... 422/186.3; 422/24
[58] Field of Search ................... 422/186.3, 24; 210/748, 760; 204/157.44, 176

[56] References Cited

U.S. PATENT DOCUMENTS

| | | | |
|---|---|---|---|
| 3,550,782 | 12/1970 | Veloz | 210/192 |
| 4,141,830 | 2/1979 | Last | 210/63 Z |
| 4,156,652 | 5/1979 | Wiest | 250/527 |
| 4,179,616 | 12/1979 | Coviello et al. | 250/527 |
| 4,189,363 | 2/1980 | Beitzel | 204/157.1 R |
| 4,204,956 | 5/1980 | Flatow | 210/87 |
| 4,230,571 | 10/1980 | Dadd | 210/760 |
| 4,534,282 | 8/1985 | Marinoza | 99/451 |
| 4,769,131 | 9/1988 | Noll et al. | 210/85 |
| 5,116,582 | 5/1992 | Cooper et al. | 422/186.3 |
| 5,126,111 | 6/1992 | Al-Ekabi et al. | 422/186.3 |
| 5,141,636 | 8/1992 | Flanagan | 210/209 |
| 5,230,792 | 7/1993 | Sauska et al. | 210/97 |
| 5,266,215 | 11/1993 | Engelhard | 210/748 |
| 5,393,419 | 2/1995 | Tiede et al. | 210/192 |
| 5,433,738 | 7/1995 | Stinson | 607/92 |
| 5,474,748 | 12/1995 | Szabo | 422/186.04 |
| 5,540,848 | 7/1996 | Engelhard | 210/748 |
| 5,567,616 | 10/1996 | Dill, II | 435/283.1 |
| 5,573,666 | 11/1996 | Korin | 210/232 |

*Primary Examiner*—Charles T. Jordan
*Assistant Examiner*—Daniel Jenkins

[57] ABSTRACT

A pathogen control system includes at least one germicidal UV tube and at least one UV transmissive tube in proximity thereto. Fluid flow in the at least one UV transmissive tube is subjected to ozone produced therein by irradiation by the germicidal UV tube, and fluid flow is controlled with no more than minor attenuation at germicidal UV radiation frequencies. A ballast power supply is connected with the germicidal UV tube.

21 Claims, 2 Drawing Sheets

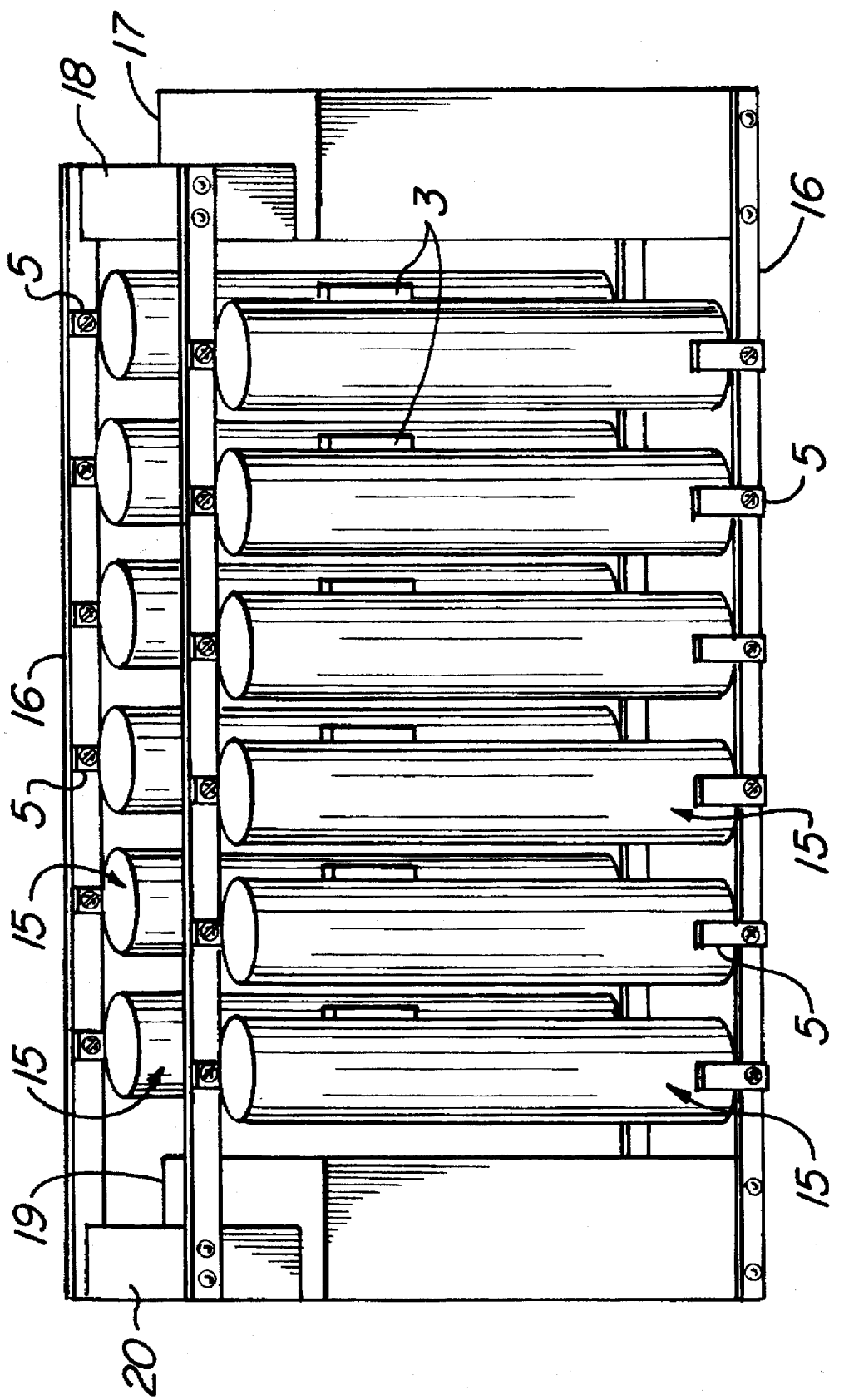

PATHOGEN CONTROL SYSTEM

BACKGROUND AND PRIOR ART

Human senses, chemicals, ultraviolet (UV) radiation, and ozone have all been used to control the deleterious effect of microorganisms. For years the only method used to check for salmonella infected chickens was through the human senses. This method proved ineffectual because of the shear volume of chickens that needed to be inspected and the lack of human senses ability to detect infected chickens which resulted in passing the bacteria to other chickens via the wash water. Chlorine has been used to treat water but it has the residual effect of bad taste and is now suspect as being a producer of carcinogens. Germicidal ultraviolet radiation is effective in controlling pathogens by being absorbed in the microorganism's DNA which prevents cell division. However, the effects of UV are attenuated by the water volume. Ozone is very effective in destroying microorganisms, although ozone generated in the electrostatic plate discharge method is very expensive, requires huge energy requirements, leaves a foul order and taste, and produces residual metal particulates. Ozone systems using multi-chambered devices and large holding tanks are exorbitantly expensive with regard to the cost of the micro-polished steel tanks and the real estate and construction costs to support these holding tanks structures.

Some applications have used UV and ozone in combination to purify water. Four such applications of related art are described below:

U.S. Pat. No. 4,156,652 is a dual chamber device that generates ozone via UV radiation in one chamber and radiates UV through liquid in the second chamber. It also bubbles the ozone within the water in the chamber. These two chambers are connected in series. The system uses a baffle plate to slow down the flow of the air and liquid.

U.S. Pat. No. 4,179,616 is a single chamber system which houses a UV tube. The UV tube is encased in a quartz sleeve. Air is pumped inside the quartz sleeve to cool the UV tube and to create ozone. The chamber is then filled with water and is radiated by UV light. The radiated water is pumped to a holding tank where ozone is bubbled up for further water purification.

U.S. Pat. No. 4,204,956 is a single chamber system which uses multiple UV lamps. Each lamp is enclosed in a quartz sleeve. Water is passed through the system and flows around the UV lamps to decontaminate the water. Oxygen is added from an external tank into the water which then creates ozone within the dissolved oxygen in the water.

U.S. Pat. No. 4,230,571 creates ozone by blowing air into a holding tank which houses three UV bulbs contained within UV permeable material. The ozone generated is pumped into the entrance port of the water flow where it kills microorganisms. The ozonated water is then flowed into the container past the UV radiation to further kill microorganisms.

The present invention provides a means to generate ultraviolate radiation and ozone in a single chamber in-flow device which alleviates the need for holding tanks. The methodology produces the desired combination effect of UV and ozone without the high energy costs, without the bad ozone oder and taste, without leaving metal particulates, and without the exorbitantly high costs of liquid storage. And the system has a unique parallel stacking design to increase sterilization capacity to any desired level.

SUMMARY

PCS is differentiated in many respects from related art:

PCS alleviates the need for a holding tank because it uses a through-put system.

The PCS uses a single chamber device and creates ozone at the same time water is being radiated by UV light.

The PCS does not require a quartz sleeve around the UV tube to protect it from the water. The PCS flows water through non-stick, UV permeable tubing where the water never actually touches the UV tube.

The PCS creates ozone within the single chamber without requiring an outside tank of oxygen. PCS ozone is generated from air pumped through the single chamber exposing it to the radiation. The PCS has the capability of introducing ozone into the liquid within the single chamber, and can ozonate outside the PCS through-put container to sterilize an external holding tank or resevoir.

The PCS chamber can be fabricated from a variety of cost effective and efficient materials, as opposed to expensive micro polished steel tanks, such as PVC, steel or aluminum, because in the PCS water never touches the chamber housing.

Other systems generate UV at 2000 to 3000 angstroms with a killing peak at 2400 angstroms. The PCS generates two killing peaks at 1850 angstroms and 2450 angstroms.

The PCS controls water flow and permits the air to flow freely. Rather than the water flow being chaotic, it is measured. Knowing the diameter of the tubing, the water pressure, and the known exposure to the UV radiation, provides a confidence that all microorganisms passing through the tubing have been killed.

The PCS, in its main embodiment, only requires one UV bulb. Additional embodiments can vary the number and size of UV blubs and the diameter of the UV permeable tubing to increase system capacity and to adapt to end user needs.

PCS does not require an internal pump to force the generated ozone into the water to be sterilized. The PCS, using a manifolded bubble up methodology, can ozonate any body of contained water (reservoirs, existing holding tanks, etc.).

The PCS can be used for water purification on any level from reservoirs to municipal water districts to emergency water sterilization in disaster situations to residential applications. Water purification can be accomplished without the cost and space requirements for building additional structures for water containment. Water can be cycled through the PCS for UV radiation and ozone treatment concurrently or singularly.

The PCS can be used for food processing including all meats, fowl, fish, eggs, fruits and vegetables to eliminate salmonella, *E. Coli* and any other bacteria. Chicken, as well as meat and fish, processors can UV radiate and ozonate the wash water for carcasses killing bacteria, preventing infected carcasses from spreading to other chickens, and reaching into carcass cavities where in the past was totally inaccessible from human inspection, UV surface radiation alone, or chemically treated water. Egg processors can use PCS to provide a bacteria free and ozone cleansing dip. Eggs submerged shortly after being laid will eliminate or minimize the salmonella contaminating the outer shell of the egg before the bacteria has a chance to migrate through the semi-permeable shell and contaminate the egg contents.

Growers and grocery stores will be able to extend shelf life of produce by spraying ozonated water on fruits and vegetables. The PCS can be used for air borne pathogen control by adapting PCS devices to air conditioning systems. Air borne pathogens can be eradicated in hospitals, airplanes, buildings and in the home.

In the medical field PCS purified water can be used instead of contaminated tap water. Doctors and dentists could wash wounds with pure and ozonated water which would cleanse the wound and kill microorganisms upon contact.

The PCS combines a method for generating both purified liquid and ozone within one enclosure without undesirable residue and without the use of costly micro polished steel holding tanks now needed to accomplished this task using current technology. The only residue left by PCS is water, oxygen and a trace of hydrogen peroxide which will not hurt people or other living things. Other technology leaves the ozone taste, metal particulates and chemical residue which can be harmful to people. In fact these kinds of residue producing systems can not be used in food processing because the FDA forbids it. The PCS is effectively lethal to microorganisms and extremely cost efficient which dramatically lowers the cost of current water purification methods; both in cost of entry and processing.

BRIEF DESCRIPTION OF THE DRAWING

FIG. 4 is an elevational view of an embodiment of the invention wherein a plurality of the device of FIG. 1 are utilized.

Figure Reference Numbers: 1 End cap, 2 Main enclosure, 3 Ballast power supply, 4 Air fitting, 5 Mounting bracket, 6 UV bulb fixture, 7 UV bulb, 8 View hole, 9 Hose—liquid output, 10 Hose—liquid input, 11 Hose—air output, 12 Wires—AC power connection for power supply, 13 Wires—power supply output to UV bulb (6), sealed into main enclosure (2), 14 Hose—air input, 15 Hose—UV transmissive, 16 Ozone valve—ozone injection into liquid.

DESCRIPTION OF THE PREFERRED EMBODIMENTS

Figure 1:
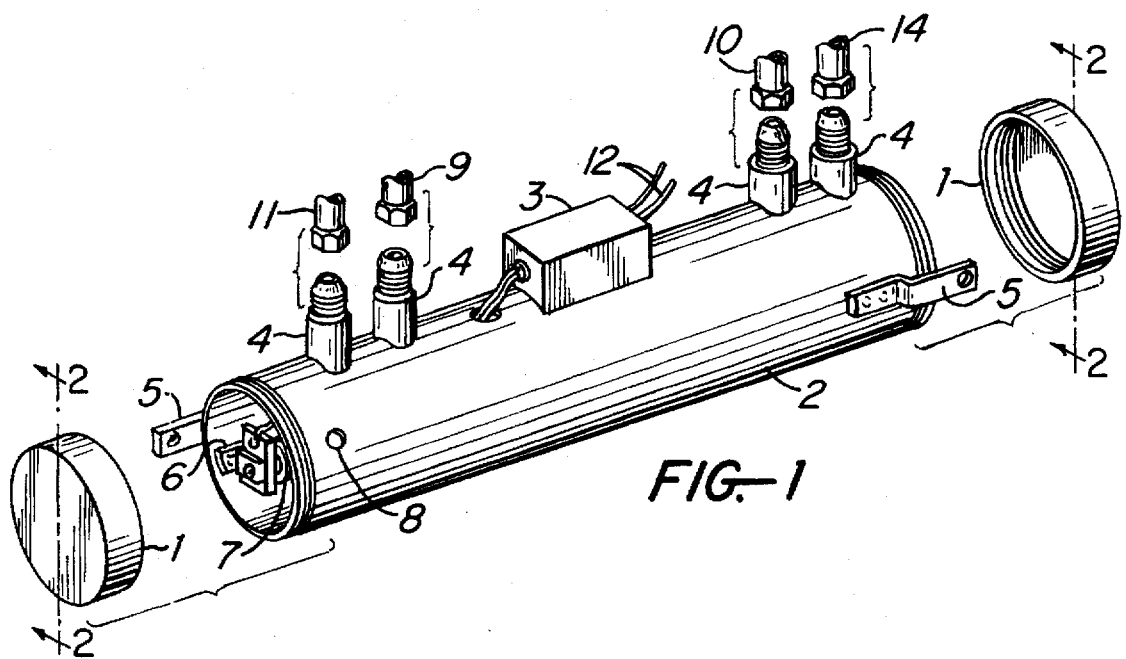
FIG. 1 shows a perspective view of the PCS exterior components.

Central to the PCS concept is the enclosure 2 shown in FIG. 1. The enclosure 2 can be formed in any shape that will accommodate the UV bulb 7 and the UV transmissive tubing 15 while still allowing some free air to flow within the system. The UV bulb 7 will be powered by the power supply 3 and wired to AC power via wires 12. Power is sent to the UV tube via output wires 13. The main enclosure 2 can be fabricated from any material that will permit an airtight or a near airtight enclosure. Enclosure sealing can be accomplished with glue, screw on end caps 1 or the end caps 1 can be secured with nuts bolts, rivets, or any other method suitable for sealing the Enclosure 2. The PCS uses a hose 10 to transport the liquid. A pump or outside pressure source is used to produce flow of both the air and the liquid to the PCS. The liquid then flows through a fitting 4 and into a UV transmissive tube 15 where it is exposed to UV radiation from the UV bulb 7. The UV bulb 7 is held in place within the enclosure by seal able hardware. The liquid itself never touches the UV bulb 7 which prevents corrosion, calcification or microbe build-up which promotes longer bulb life and easier maintainability. The tubing 15 can be fabricated from any material that will allow transmission of UV light through it; plastic or any other UV transmissive material.

Figure 2:
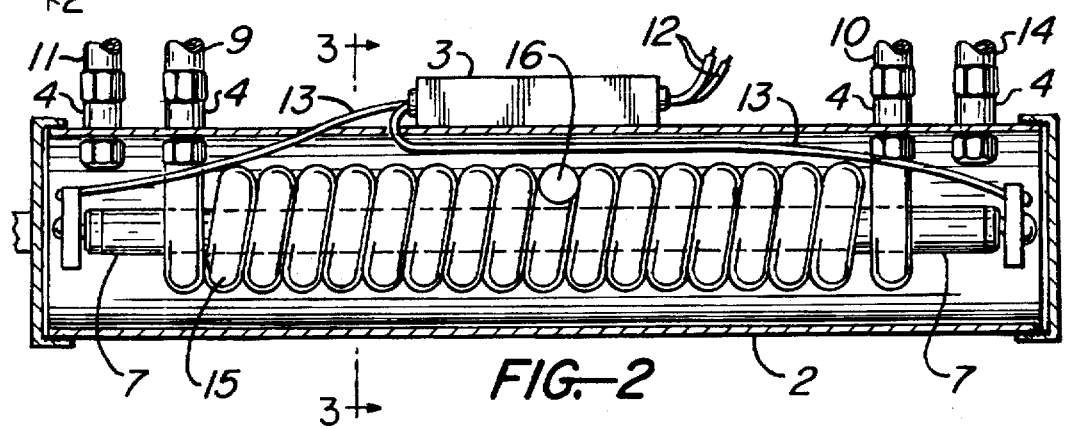
FIG. 2 illustrates a cross sectional, cut-away view of PCS internal components.
Figure 3:
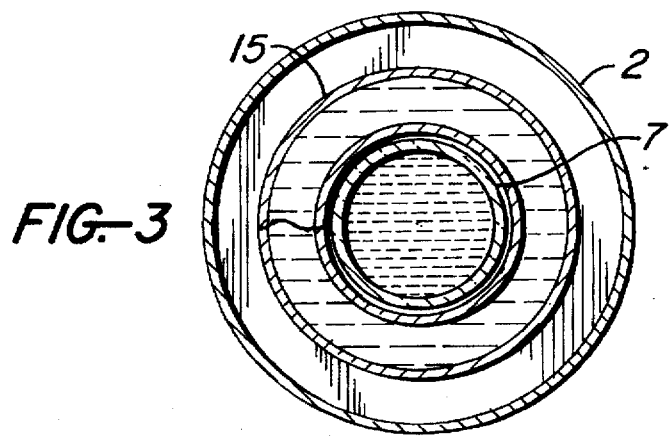
FIG. 3 displays view AA of FIG. 2.

The UV transmissive tubing 15 can be coiled around the UV bulb 7, run parallel to it or placed in any manner that allow exposure of the UV bulb 7 and the liquid within the transmissive tubing 15 to the UV radiation. An example of coiled UV transmissive tubing 15 is illustrated in FIG. 2. The PCS can also contain an ozone valve 16 which will allow ozone produced by the UV radiation to be absorbed within the liquid flowing through the PCS which provides additional pathogenic control of microorganisms while lowering liquid turbidity.

The UV bulb 7 used within the PCS enclosure 2 may be any currently manufactured or yet to be manufactured UV bulb. Different sizes and shapes of UV bulbs will vary as a function of different system application to which the PCS will be adapted.

The PCS is designed to produce ozone simultaneously with UV radiation. The ozone is produced by exposing air in the enclosure 2 to the UV radiation. As the UV radiation energy reacts with the oxygen in the air it forms ozone. This ozone can be flowed in one or both of two locations. It will flow through the air output fitting 4 and the air output tube 11. As it flows through the ozone valve 16 it aids in eliminating microorganisms within the liquid as it passes through the PCS. As the ozone flows through the air output fitting 4 and the hose 10 it can be sent to an outside tank holding the liquid, or material to be sterilized, where the ozone pumped from the PCS will accomplish this purification. Based on the requirement of the end user's sterilization objectives, the PCS can generate UV, ozone or both.

The capacity of the liquid flowing through the PCS can be controlled. For example, flow can be increased by using a longer UV tube which allows more than one UV transmissive coil to be wrapped around the UV tube. This increase in flow can be accommodated by using more fittings or by the use a manifold to distribute water inflows and outflows. Liquid flow capacity can also be increased by adding more than one UV tube to the PCS again through the use of additional fitting and hoses. Adding more UV tubes also increases ozone production. Another method the PCS uses to increase water volume is to increase the diameter of the UV transmissive tube thereby allowing more liquid to flow within any one of the transmissive tubes.

The PCS is designed for both parallel operations and device stacking. Mounting bracket 5 allows many systems to be rack mounted where the gas and liquid inputs and outputs can be connected together via a manifold or any other viable connection method which allows the PCS to be expanded to virtually any size system to accommodate any desired capacity. FIG. 4 shows such an arrangement. A plurality of individual modules 15, each having a power supply 3 and an ozone valve 16, are mounted on a mounting rack. Input water is supplied to a manifold 17 and input air enters a manifold 18, and both passes under appropriate pressure to each module 15. Flows of sterilized liquid and air from the modules 15 are recombined respectively in output air manifold 20 and in water manifold 19.

Total systems handling in excess of one hundred million gallons of liquid per day can be fabricated. Concurrently, system downtime is minimized because if any one of the devices require maintenance, the balance of the total system will remain in operation. For an example, if the total system contains 100 single PCS devices and one of the devices fail, the total system will still operate at 99% efficiency while the failed device is being replaced. Using the remove and replace method of maintenance, full operation can be re-attained within minutes. A view hole 8 is placed in the enclosure 2 to enable viewing and troubleshooting of system operation.

What is claimed is:

1. A pathogen control system comprising:
   at least one germicidal UV tube,
   at least one UV transmissive tube in proximity to said at least one germicidal UV tube,
   means for providing fluid flow through the UV transmissive tube, and
   means for applying to the fluid flow in the UV transmissive tube ozone produced therein by irradiation by the germicidal UV tube to further sterilize the liquid.

2. A pathogen control system according to claim 1, wherein:
   said UV tube is spirally disposed about said UV tube.

3. A system according to claim 1, wherein said means for applying ozone to the liquid flow comprises:
   valve means connected with said at least one UV transmissive tube for introduction of ozone formed therein to liquid flow.

4. A system according to claim 1, and further including:
   means for transferring to exterior holding means said ozone produced by irradiation of liquid flow.

5. A system according to claim 1, and further including:
   ballast power supply means connected with the germicidal UV tube and tuned for germicidal efficiency.

6. A system according to claim 1, and further including:
   means for providing controlled measured liquid flow with no more than minor attenuation at germicidal UV radiation frequencies.

7. A system according to claim 6 wherein there is no more than minor attenuation at the germicidal frequencies of 184.9 and 254 nanometers.

8. A system according to claim 1, and further including:
   means for quickly energizing said at least one germicidal UV tube for quick germicidal radiation output.

9. A system according to claim 1 wherein said control system is adapted for portability for application of sterilized liquid at selected sites.

10. A system according to claim 1 wherein said control system is adapted for the spraying of sterilized liquid on food items.

11. A system according to claim 10 wherein the food items may be any of fruits, vegetables, meats, fowls and fish.

12. A system according to claim 1 wherein the system is adapted to provide sterilized air at medical treatment sites.

13. A system according to claim 12 wherein said sterilized air is provided via an air conditioning system.

14. A pathogen control system comprising:
   a plurality of germicidal UV tubes,
   a plurality of transmissive UV tubes in proximity respectively to respective germicidal UV tubes,
   means for energizing the germicidal UV tubes to produce sterilizing radiation,
   means connected with at least certain of the transmissive UV tubes for passage thereto of a supply of water and air flow, and
   means connected with said transmissive UV tubes to receive sterilized liquid therefrom and to communicate said sterilized liquid exterially of the tubes.

15. A pathogen control system according to claim 14, and further including:
   means for applying to the fluid flow in at least some of the UV transmissive tubes ozone produced therein by irradiation by the germicidal UV tubes to further sterilize the liquid.

16. A system according to claim 14, and further including ballast power supply means connected with the germicidal UV tubes and tuned for germicidal efficiency.

17. A system according to claim 14, and further including:
   means for providing controlled measured liquid flow with no more than minor attenuation at germicidal UV radiation frequencies.

18. A system according to claim 14, and further including:
   means for quickly energizing at least some of said germicidal UV tubes for quick germicidal radiation output.

19. A system according to claim 15, and further including:
   means for transferring to exterior holding means said ozone produced by irradiation of liquid flow.

20. A system according to claim 14, wherein the system is adapted to provide sterilized air at medical treatment sites.

21. A system according to claim 14, wherein said control system is adapted for the spraying of sterilized liquid on food items.

\* \* \* \* \*